(12) United States Patent
Bushman et al.

(10) Patent No.: US 7,438,707 B2
(45) Date of Patent: Oct. 21, 2008

(54) ABSORBENT ARTICLES WITH ABSORBENT PAD GAPPING

(75) Inventors: Lisa Bushman, Kaukauna, WI (US);
Kay L. Konieczny, Appleton, WI (US);
Brenda M. Nelson, Appleton, WI (US);
Lisa L. Nickel, Neenah, WI (US)

(73) Assignee: Kimberly-Clark Worldwide, Inc, Neenah, WI (US)

( * ) Notice: Subject to any disclaimer, the term of this patent is extended or adjusted under 35 U.S.C. 154(b) by 1393 days.

(21) Appl. No.: 10/035,650

(22) Filed: Dec. 28, 2001

(65) Prior Publication Data

US 2003/0125697 A1 Jul. 3, 2003

(51) Int. Cl.
*A61F 13/15* (2006.01)

(52) U.S. Cl. .............. 604/385.22; 604/385.16; 604/385.23; 604/378; 604/385.25; 604/385.3

(58) Field of Classification Search ............ 604/385.01, 604/385.16, 385.22, 385.23, 378, 385.25, 604/385.3
See application file for complete search history.

(56) References Cited

U.S. PATENT DOCUMENTS

| | | | | |
|---|---|---|---|---|
| 4,710,187 A | * | 12/1987 | Boland et al. | .......... 604/385.22 |
| 4,846,825 A | * | 7/1989 | Enloe et al. | ............ 604/385.22 |
| 4,895,568 A | | 1/1990 | Enloe | |
| 5,269,775 A | * | 12/1993 | Freeland et al. | ........ 604/385.22 |
| 5,403,267 A | * | 4/1995 | Pearce et al. | .................. 602/8 |
| 5,425,726 A | | 6/1995 | Shimizu et al. | |
| 5,575,783 A | | 11/1996 | Clear et al. | |
| 5,593,400 A | | 1/1997 | O'Leary | |
| 5,885,264 A | | 3/1999 | Matsushita | |
| 5,891,124 A | | 4/1999 | Normura et al. | |
| 6,020,535 A | | 2/2000 | Blenke et al. | |
| 6,160,200 A | | 12/2000 | Ehrnsperger et al. | |
| 6,169,225 B1 | | 1/2001 | Otsubo | |
| 6,471,682 B2 | * | 10/2002 | Kashiwagi | ............. 604/385.27 |
| 6,702,801 B2 | * | 3/2004 | Van Gompel et al. | .. 604/385.22 |
| 2002/0010454 A1 | | 1/2002 | Van Gompel et al. | |

FOREIGN PATENT DOCUMENTS

| | | |
|---|---|---|
| EP | 0 357 298 A3 | 3/1990 |
| EP | 0 382 022 B1 | 1/1994 |
| EP | 0 581 044 B1 | 5/1998 |
| EP | 0 661 031 B1 | 4/2001 |
| GB | 2 340 403 A | 2/2000 |
| WO | WO 97/07764 | 3/1997 |
| WO | WO 02/34185 A1 | 5/2002 |

* cited by examiner

*Primary Examiner*—Jacqueline F. Stephens
(74) *Attorney, Agent, or Firm*—Armstrong Teasdale, LLP

(57) ABSTRACT

An absorbent article constructed to isolate skin from absorbed moisture and promote ventilation. The article, which has particular application in the form of an absorbent garment worn to capture body wastes, has an absorbent body and liquid impermeable outer cover which stretch under the weight of the loaded absorbent body. A bodyside liner between the absorbent body and the skin of the wearer stretches, but to a lesser extent than the absorbent body and the outer cover. Accordingly, a gap between the bodyside liner and the absorbent body is created. The gap removes the moisture ladened absorbent body from the skin and forms a gap which helps air and vapor to circulate around the skin, promoting dryness.

25 Claims, 4 Drawing Sheets

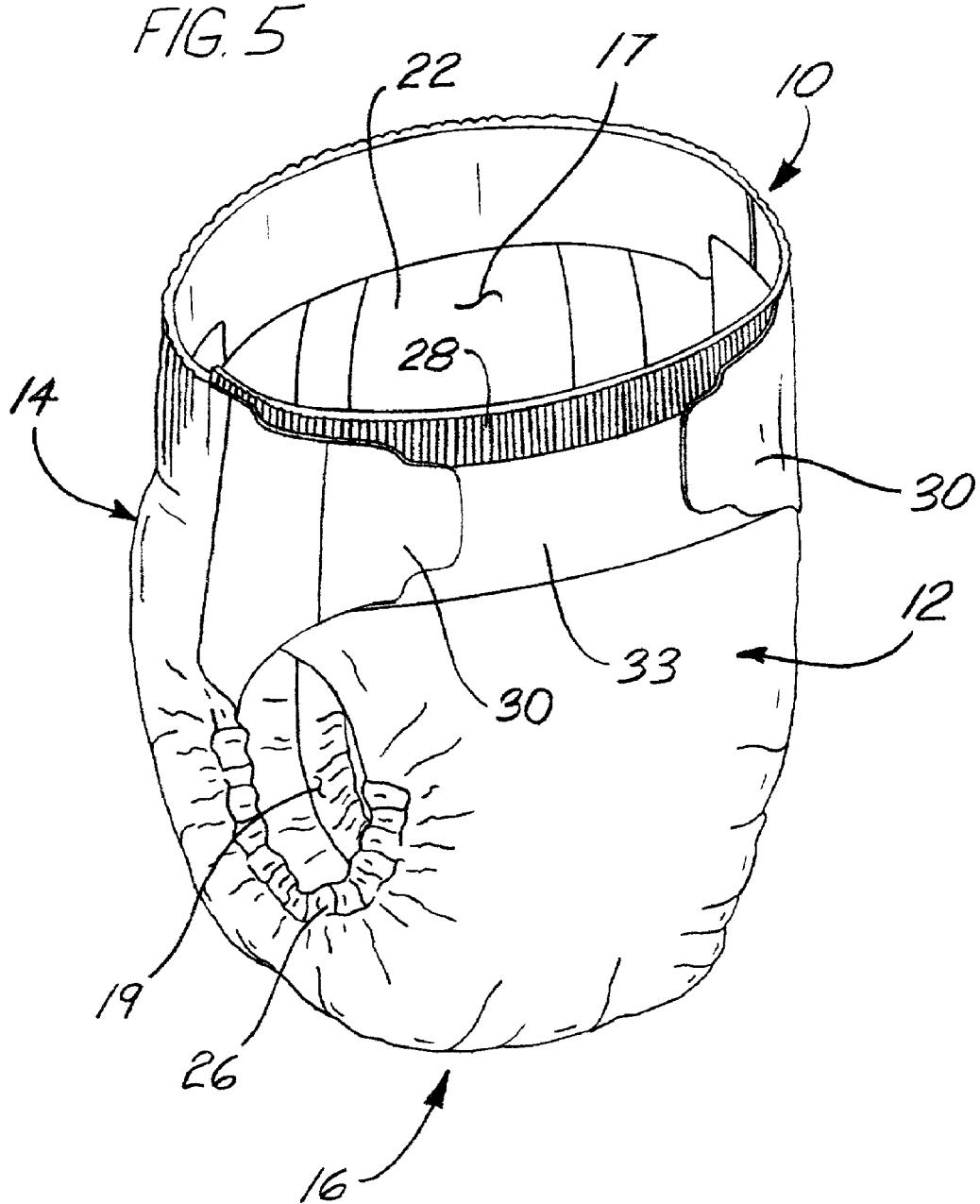

ABSORBENT ARTICLES WITH ABSORBENT PAD GAPPING

FIELD OF THE INVENTION

The present invention relates to absorbent articles, desirably disposable absorbent articles which facilitate maintenance of skin dryness.

BACKGROUND OF THE INVENTION

The stratum corneum is the outer-most layer of the skin and is responsible for regulating skin water levels and functioning as a barrier against chemicals and other stress agents found in the environment. The complex arrangement of lipids in the intercellular space of the stratum corneum is responsible for the establishment of normal barrier function. Multi-layered structures of cholesterol, ceramides and fatty acids, as well as some other minor lipids, provide the major barrier to the transport of substances into or through the skin. The overall structure of the stratum corneum acts as the frontline barrier to the skin. The link between skin barrier function and skin health is apparent from the skin inflammation caused by lipid extraction from the skin. That is, when skin barrier function is impaired, the other layers of the skin can be injured and have a response to that injury in the form of inflammation.

Absorbent articles such as diapers, training pants, incontinence products and feminine care products are worn such that they are in direct contact with the skin of the wearer. An unavoidable consequence of the use of absorbent articles is that the skin is exposed more directly to biological insults. Consequently, the barrier function of the skin covered by the absorbent article is put at risk. Biological fluids, such as urine, may contain a variety of components that can damage the skin barrier. Diaper dermatitis is a genre of skin conditions that, in large part, originate from impaired skin barrier function. Impairment of the skin barrier can result from a variety of factors, including: increased skin hydration due to the occlusion of the skin caused by diapers. Excessive hydration of the skin has a negative effect on the skin barrier. The hydration level of diapered skin, for example, may reach between five to ten times that of undiapered skin. It is believed to be frequent contact of diapered skin with urine contributes to increased skin hydration. Increased skin hydration disrupts skin lipid organization in the stratum corneum. This disruption may increase the permeability of the skin to irritants from feces and urine, thus increasing the risk of skin inflammation.

Disposable absorbent articles such as diapers, training pants, adult incontinence products, absorbent under pants, feminine care products and nursing pads have been used to absorb body fluids and leave the skin dry. Disposable absorbent articles of this type generally include a liquid impermeable outer cover, an absorbent body, and a liquid permeable bodyside liner. The bodyside liner comes into contact with the wearer's skin and is interposed between the skin and the absorbent body. Generally, the bodyside liner is not configured to retain liquid, which passes through the bodyside liner to the absorbent body where it is retained. However, the location of the absorbent body immediately adjacent the bodyside liner can cause the skin to be hydrated by moisture (e.g., urine) which is held in the absorbent body immediately adjacent to the bodyside liner, or at a minimum inhibit adequate ventilation of the skin. The presence of these conditions is believed to be detrimental to skin health.

SUMMARY OF THE INVENTION

In response to the difficulties and problems discussed above, new absorbent article constructions have been found which provide improved breathability and overall reduction of skin hydration for improved skin health.

In one aspect of the present invention, an absorbent article comprises an outer cover adapted to stretch upon application of a load by a first amount. A liquid and gas permeable bodyside liner defining a bodyfacing surface and generally superposed and coextensive with the outer cover, is adapted to stretch upon application of the load by a second amount. An absorbent body located between the bodyside liner and the outer cover is generally movable with the outer cover upon stretching of the outer cover. The first amount of stretch of the outer cover is greater than the second amount of stretch of the bodyside liner whereby a gap is formed between the bodyside liner and the absorbent body facilitating the flow of air and vapor through the bodyside liner in a loaded condition of the absorbent body.

In another aspect of the present invention, an absorbent garment for capturing human waste when worn comprises a liquid impermeable outer cover adapted to stretch upon application of a load by a first amount. A liquid and gas permeable bodyside liner generally superposed and coextensive with the outer cover is adapted to stretch upon application of the load by a second amount. The bodyside liner comprises a sheet of liquid and gas permeable material defining a bodyfacing surface, and plural cords of resilient elastic material on a side of the sheet opposite the bodyfacing surface, the cords applying a resilient force in opposition to stretching of the sheet. An absorbent body located between the bodyside liner and the outer cover is generally movable with the outer cover upon stretching of the outer cover. The first amount of stretch of the outer cover is greater than the second amount of stretch of the bodyside liner whereby a gap is formed between the bodyside liner and the absorbent body facilitating the flow of gas through the bodyside liner in a loaded condition of the absorbent body.

BRIEF DESCRIPTION OF THE DRAWINGS

FIG. 5 is a perspective view of the diaper shown as worn.

Corresponding reference characters indicate corresponding parts throughout the several views of the drawings.

DEFINITIONS

Figure 1:
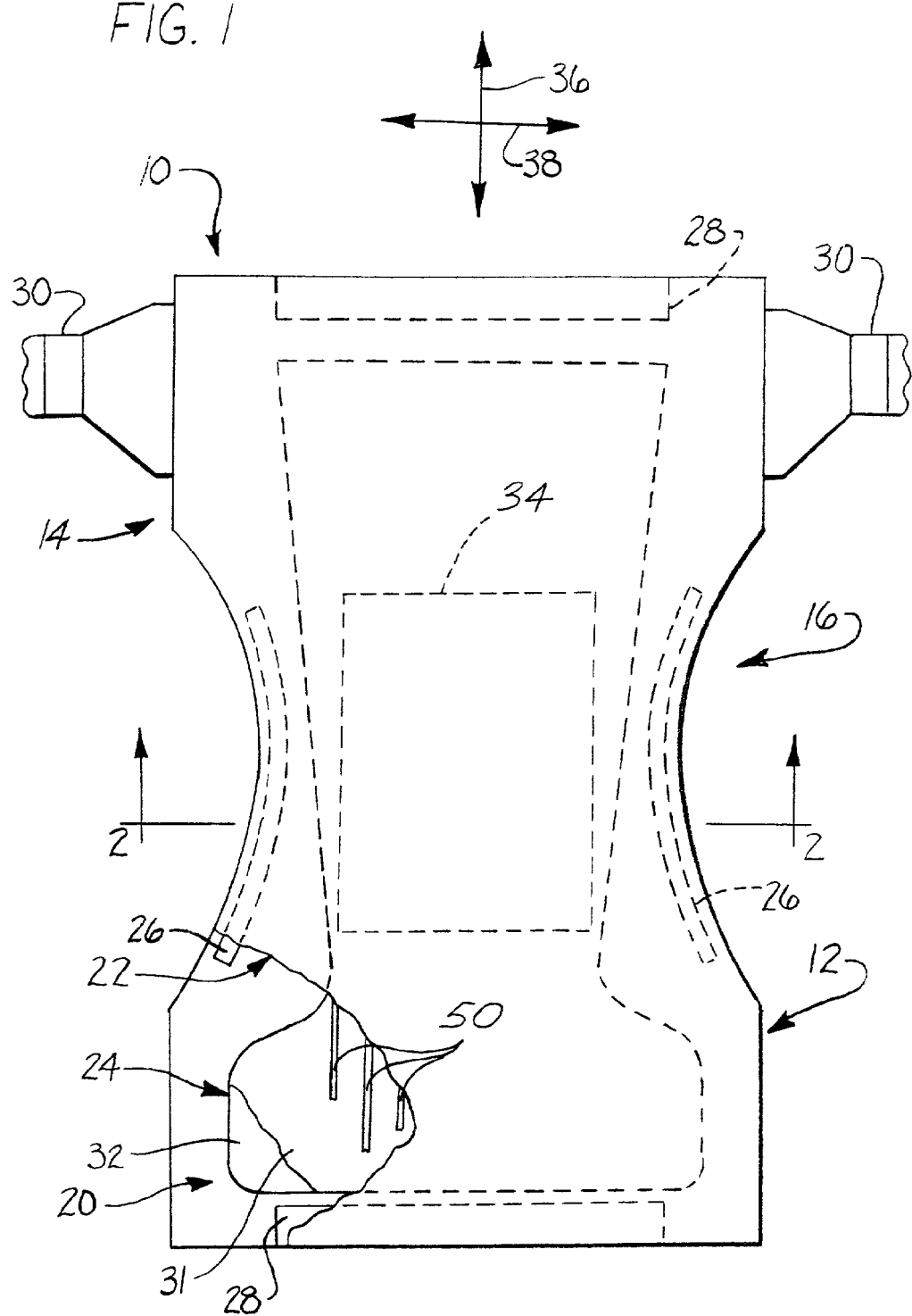
FIG. 1 is a plan view of a diaper constructed according to the principles of the present invention with the diaper shown unfastened and laid flat and portions of the diaper broken away to reveal internal construction thereof.

Within the context of this specification, each term or phrase below will include the following meaning or meanings:

(a) "Bonded" refers to the joining, adhering, connecting, attaching, or the like, of two elements. Two elements will be considered to be bonded together when they are bonded directly to one another or indirectly to one another, such as when each is directly bonded to intermediate elements.

(b) "Film" refers to a thermoplastic film made using a film extrusion and/or foaming process, such as a cast film or blown film extrusion process. The term includes apertured films, slit films, and other porous films which constitute liquid transfer films, as well as films which do not transfer liquid.

(c) "Hydrophilic" describes fibers or the surfaces of fibers which are wetted by aqueous liquids in contact with the fibers.

The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 degrees are designated "wettable" or hydrophilic, and fibers having contact angles greater than 90 degrees are designated "nonwettable" or hydrophobic.

(d) "Layer" when used in the singular can have the dual meaning of a single element or a plurality of elements.

(e) "Liquid impermeable," when used in describing a layer or multi-layer laminate means that liquid body waste, such as urine, will not pass through the layer or laminate, under ordinary use conditions, in a direction generally perpendicular to the plane of the layer or laminate at the point of liquid contact.

(f) "Liquid permeable" refers to any material that is not liquid impermeable.

(g) "Meltblown" refers to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameters. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

(h) "Non-woven" and "non-woven web" refer to materials and webs of material which are formed without the aid of a textile weaving or knitting process.

(i) "Pliable" refers to materials which are compliant and which will readily conform to the general shape and contours of the wearer's body.

(j) "Spunbond" refers to small diameter fibers which are formed by extruding molten thermoplastic material as filaments from a plurality of fine capillaries of a spinnerette having a circular or other configuration, with the diameter of the extruded filaments then being rapidly reduced by a conventional process such as that described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, more particularly, between about 0.6 and about 10.

(k) "Superabsorbent" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

(l) "Thermoplastic" describes a material which softens when exposed to heat and which substantially returns to a non-softened condition when cooled to room temperature.

(m) "Stretchable", refers to materials which are either elastic or extensible, that is materials which when elongated in one or more dimensions either exert a force tending to move the material at least partially to its original dimensions (elastic), or which remain in the elongated configuration (extensible).

DETAILED DESCRIPTION OF THE INVENTION

The present invention is directed to solving problems related to protecting the skin barrier by preserving the opportunity for adequate skin ventilation for areas of the skin which are close (i.e., nearly immediately opposite) an absorbent body of an absorbent article of the type worn about the lower torso and upper legs to capture human waste.

FIG. 1 is a representative plan view of an absorbent article in the form of a disposable diaper 10 in a flat-out, uncontracted state (i.e., with all elastic induced gathering and contraction removed). As used herein, an absorbent article refers to an article which may be placed against or in proximity to the body (i.e., contiguous to the body) of the wearer to absorb and contain various liquid waste discharged from the body. Such articles are intended to be disposed of after a limited period of use instead of being laundered or otherwise restored for reuse. It is contemplated that the principles of the present invention have application in other garments (including reusable garments) and absorbent articles (not shown). For example, training pants and other infant and child care products, adult incontinence garments and other adult care products, sanitary napkins and other feminine care products and the like, as well as surgical bandages and sponges.

The diaper 10 includes an anterior region 12, a posterior region 14, and a crotch region 16 that interconnects the anterior and posterior regions 12 and 14. The anterior and posterior regions 12 and 14 include the portions of the diaper 10 that are constructed to extend substantially over the wearer's front and rear abdominal regions, respectively, during use. The crotch region 16 of the diaper 10 includes the portion of the diaper 10 that is constructed to extend through the wearer's crotch between the legs. The anterior, posterior and crotch regions 12, 14, 16 are shaped and arranged so that, as worn on the body, the diaper 10 defines a central waist opening 17 and a pair of leg openings 19 (FIG. 5).

The diaper 10 further includes a vapor permeable outer cover 20, a liquid permeable bodyside liner 22 positioned in facing relation with the outer cover, and an absorbent body 24, which is located between the outer cover and the bodyside liner. The outer cover 20 defines, in the illustrated embodiment, the length and width of the diaper 10. The absorbent body 24 has a length and width that are less than the length and width of the outer cover 20. Thus, marginal portions of the diaper 10, such as marginal sections of the outer cover 20, extend past the terminal edges of the absorbent body 24. In the illustrated embodiment, the outer cover 20 extends outwardly beyond the terminal marginal edges of the absorbent body 24 to form side margins and end margins of the diaper 10. The bodyside liner 22 is generally coextensive with the outer cover 20 but may optionally overlie an area that is larger or smaller than the area of the outer cover 20, as desired. In other words, the bodyside liner 22 is preferably in superposed relation with the outer cover 20 but may not necessarily be coextensive with the outer cover. The outer cover 20 and bodyside liner 22 are intended to face the garment and body of the wearer, respectively, while in use.

To provide improved fit and to help reduce leakage of body exudates from the diaper 10, the diaper side margins and end margins may be elasticized with suitable elastic members, such as single or multiple strands of elastic material. The elastic strands may be composed of natural or synthetic rubber and may optionally be heat shrinkable or heat elasticizable. For example, as representatively illustrated in FIG. 1, the diaper 10 may include leg elastics 26 which are constructed to operably gather and shirr the side margins of the diaper 10 to closely fit around the legs of the wearer to reduce leakage and provide improved comfort and appearance. Similarly, waist elastics 28 can be employed to elasticize the end margins of the diaper 10 to provide elasticized waists. The waist elastics 28 are configured to operably gather and shirr the waist sections to provide a resilient, comfortably close fit around the waist of the wearer. The elastic members are illustrated in their uncontracted, stretched condition in FIG. 1 for the purpose of clarity.

Fasteners, such as hook and loop fasteners 30, are employed to secure the diaper 10 on the body of a child or other wearer of the diaper. Alternatively, other fasteners, such as buttons, pins, snaps, adhesive tape fasteners, cohesives, mushroom-and-loop fasteners, or the like (not shown), may be employed. Additionally, more than two fasteners can be provided, particularly if the diaper 10 is to be provided in a prefastened configuration.

A loop element (not shown) may be provided directly by the outer cover 20 of the diaper 10 to provide a "fasten anywhere" mechanical fastening system for improved fastening. Alternatively, the diaper 20 may include one or more attachment panels 33 (shown as a single panel in FIG. 5) to which the fasteners 30 are configured to releasably engage. For example, when the fasteners 30 are hook fasteners located in the posterior region 14 near the waist opening, the diaper may include a corresponding attachment panel such as a complementary loop element on the outward facing surface in the front waist section 22. The attachment panels may be provided by a woven fabric, a nonwoven fabric, a knitted fabric, a perforated or apertured layer, and the like, as well as combinations thereof. For example, a suitable material for the attachment panel can be composed of a 2 bar, warp knit fabric of the type available from Guilford Mills, Inc., Greensboro, N.C. under the trade designation #34285, as well other of knit fabrics.

The disposable diaper 10 may also include a pair of containment flaps (not shown) which are configured to provide a barrier to the lateral flow of body exudates. The containment flaps may be located along the laterally opposed side edges of the diaper 10 adjacent the side edges of the absorbent body 24. Each containment flap typically defines an unattached edge which is configured to maintain an upright, perpendicular configuration in at least the crotch region 16 of the diaper 10 to form a seal against the wearer's body. The containment flaps may extend longitudinally along the entire length of the absorbent body 24 or may only extend partially along the length of the absorbent body. When the containment flaps are shorter in length than the absorbent body 24, the containment flaps can be selectively positioned anywhere along the side edges of the diaper 10 in the crotch region 16. Preferably, the containment flaps extend along the entire length of the absorbent body 24 to better contain the body exudates.

Such containment flaps are generally well known to those skilled in the art. For example, suitable constructions and arrangements for containment flaps are described in U.S. Pat. No. 4,704,96 issued Nov. 3, 1987, to K. Enloe, the disclosure of which is hereby incorporated by reference.

The absorbent body 24 of the illustrated embodiment includes three layers, however it is to be understood that the body may have one, two or more than three layers without departing from the scope of the present invention. A central absorbent layer 31 of the absorbent body 24 preferably includes hydrophilic fibers and superabsorbent particles, as described more fully below. The absorbent body 24 further includes a ventilation layer 32 located between the central absorbent layer 31 and the outer cover 20 to insulate the outer cover 20 from the absorbent body 24, to improve air circulation and to effectively reduce the dampness of the garment facing surface of the outer cover 20. The ventilation layer 32 also assists in distributing fluid exudates to portions of the absorbent body 24 that do not directly receive an insult. The absorbent body 24 also includes a surge management layer 34 located between the bodyside liner 22 and the central absorbent layer 31 to prevent pooling of the liquid exudates and further improve air exchange and distribution of the liquid exudates within the diaper 10.

The diaper 10 of the illustrated embodiment has a generally hourglass or "I" shape. However, the diaper 10 may have other shapes, such as a rectangular shape or a T-shape without departing from the scope of the present invention. For purposes of this description, a longitudinal direction 36 and a lateral direction 38 have been indicated in FIG. 1. Other suitable diaper components (not shown) that may be incorporated on absorbent articles of the present invention include waist flaps, elastomeric side panels, and the like which are generally known to those skilled in the art. Likewise, if the diaper 10 is to be sold in a prefastened condition, the diaper 10 may have passive bonds (not shown) that join the posterior region 14 with the anterior region 12. Examples of diaper configurations suitable for use in connection with the instant application that may include other diaper components suitable for use on diapers are described in U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al., and U.S. Pat. No. 5,509,915 issued Apr. 23, 1996 to Hanson et al., the disclosures of which are herein incorporated by reference.

The various components of the diaper 10 are integrally assembled together employing a suitable form of attachment, such as adhesive, sonic bonds, thermal bonds or combinations thereof. In the illustrated embodiment, the outer cover 20 and absorbent body 24 are attached to each other with lines of adhesive 39, such as a hot melt or pressure-sensitive adhesive. The bodyside liner 22 is also connected to the outer cover 20 and may also be connected to the absorbent body 24 using the same forms of attachment. However, the bodyside liner 22 is free of fixed connected to the outer cover and absorbent body 24 in the crotch region 16. The bodyside liner 22 may be connected to the outer cover 20 at the lateral (38) edge margins of the crotch region 16, but at least the central portion is free of such connection. Rather than being entirely free of such connection, the bodyside liner 22 may be connected to the absorbent body 24 and/or outer cover 20 in the crotch region 16 by a light adhesive which will break away in use. Preferably, connection of the bodyside liner 22 to the outer cover 20 is limited to overlying peripheral edge margins of the two to promote independent stretching movement of the liner and cover relative to each other as will be described hereinafter.

Figure 4:
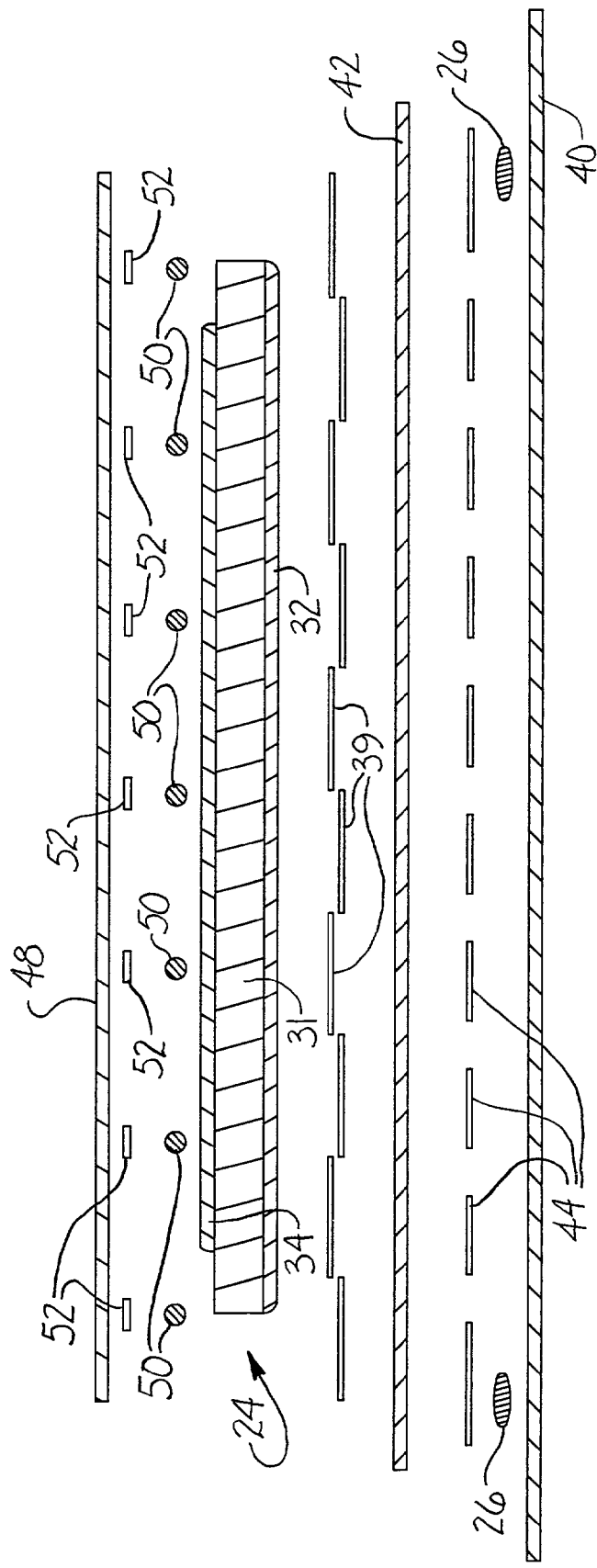
FIG. 4 is a schematic, separated cross-section taken transversely through a crotch region of the diaper.

The outer cover 20 should be stretchable and may or may not be somewhat elastic. Preferably, the outer cover 20 is extensible such that once stretched under the weight of the absorbent padded loaded by urine, it will not move substantially back toward its original position. For example, the outer cover 20, constructed of materials describe hereinafter, can be stretched to 25% to 150% of its original length with a very low force required to extend. More preferably, the outer cover 20 can be stretched 50% to 100% of its original length and most preferably the outer cover can be stretched to about 50% of its original length under a low stretching force. For example, in one embodiment, 25% elongation is achieved upon application of a force of in the range of about 30 g/in to about 200 g/in, more preferably the force required is between about 70 g/in and 150 g/in and most preferably the force required to produce such elongation is about 100 g/in. As shown in FIG. 4, the outer cover is a multi-layered laminate structure of which at least one of the layers is liquid impermeable. For example, the outer cover 20 of the illustrated embodiment is of two-layer construction, including an outer layer 40 constructed of a vapor and liquid permeable material and an inner layer 42 constructed of a liquid impermeable material joined together in a suitable manner such as by a laminate adhesive 44. It is understood that the outer cover 20 may instead be constructed of a single layer of impermeable material (not shown) without departing from the scope of this invention.

The liquid permeable outer layer 40 of the outer cover 20 can be any suitable stretchable material and is desirably one which provides a generally cloth-like texture. One example of such a material is a 0.4 osy (ounce per square yard) or 14 gsm (grams per square meter) spunbond polypropylene non-woven web. Preferably the outer layer 40 is necked to 35% to 45%. The outer layer 40 may also be constructed of the same materials from which the bodyside liner 22 is constructed as described later herein. Also, while it is not a necessity for the outer layer 40 of the outer cover 20 to be liquid permeable, it is desired that it have a cloth-like texture.

The liquid impermeable inner layer 42 of the outer cover 20 can be either vapor permeable (i.e., "breathable") or vapor impermeable. The inner layer 42 is desirably manufactured from a thin plastic film, although other flexible liquid impermeable materials may also be used. The liquid impermeable inner layer 42 (or the liquid impermeable outer cover 20 where the outer cover is of a single-layer construction) inhibits liquid body waste from leaking out of the pants and wetting articles, such as bed sheets and clothing, as well as the wearer and care giver. The film inner layer 42 is preheated, stretched lengthwise to about 3 to 5 times its original length and annealed to form micropores. The inner layer 42 is then laminated to the spunbond nonwoven web forming the outer layer 40. Thus, in this preferred embodiment, the inner layer 42 is breathable, which desirably augments other features of the present invention in the promotion of skin health, as described more fully hereinafter.

As stated above, the extensible outer cover 20 is configured to be substantially impermeable to liquid. For example, the outer cover 20 can have a construction that is capable of supporting a selected hydrohead of water substantially without leakage therethrough. A suitable technique for determining the resistance of a material to liquid penetration is Federal Test Method Standard FTMS 191 Method 5514, 1978, or an equivalent thereof. Since the outer cover 20 is extensible, a layer of nylon net material having a thickness of about 0.1 mm may be needed to support the outer cover material for this test. The net material may be provided by nylon threads arranged in a hexagonal or honeycomb-like pattern with openings approximately 4 mm across. For example, the net material may be purchased from Wal-Mart Stores under the trade designation T-246. The net material is liquid pervious and does not significantly affect the hydrohead values obtained. The extensible outer cover 20 is sufficiently impermeable to liquid and semi-liquid materials to substantially prevent the undesired leakage of waste materials, such as urine and feces. For example, the extensible outer cover 20 can desirably support a hydrohead of at least about 45 centimeters (cm) substantially without leakage. The extensible outer cover 20 can alternatively support a hydrohead of at least about 55 cm, and optionally, can support a hydrohead of at least about 60 cm, or more, to provide improved benefits.

The extensible outer cover 20 can be composed of various materials that can provide the desired properties set forth herein. For example, the extensible outer cover 20 can be composed of a necked fabric, a creped fabric, a crimped fiber fabric, an extendable fiber fabric, a bonded-carded fabric, a micro-pleated fabric, polymer films or the like, as well as combinations thereof. The fabrics may be woven or nonwoven materials, such as spunbond fabrics. In the illustrated embodiment, the extensible outer cover 20 includes two layers (40, 42), but may include a greater number or only a single layer. In the illustrated embodiment, the extensible outer cover 20 may be a necked laminate in which the outer layer 40 is formed from a neckable fabric laminated to the inner layer 42 formed from an extendable film material wherein the necked laminate is extensible in at least one direction. However, it is to be understood that a laminate which is not necked falls within the scope of the present invention. The term "fabrics" is used to refer to all of the woven, knitted and nonwoven fibrous webs.

As used herein, the term "neck" or "neck stretch" interchangeably means that the fabric is drawn such that it is extended under conditions reducing its width or its transverse dimension by drawing and elongating to increase the length of the fabric. The controlled drawing may take place under cool temperatures, room temperature or greater temperatures and is limited to an increase in overall dimension in the direction being drawn up to the elongation required to break the fabric. The necking process typically involves unwinding a sheet from a supply roll and passing it through a brake nip roll assembly driven at a given linear speed. A take-up roll or nip, operating at a linear speed higher than the brake nip roll, draws the fabric and generates the tension needed to elongate and neck the fabric. U.S. Pat. No. 4,965,122 entitled REVERSIBLY NECKED MATERIAL, by M. T. Morman which issued Oct. 23, 1990, the entire disclosure of which is hereby incorporated by reference, discloses a process for providing a reversibly necked nonwoven material which may include necking the material, then heating the necked material, followed by cooling.

As used herein, the term "neckable material or layer" means any material which can be necked such as a nonwoven, woven, or knitted material. As used herein, the term "necked material" refers to any material which has been drawn in at least one dimension, (e.g. lengthwise), reducing the transverse dimension, (e.g. width), such that when the drawing force is removed, the material can be pulled back to its original width. The necked material typically has a higher basis weight per unit area than the un-necked material. When the necked material is pulled back to its original un-necked width, it should have about the same basis weight as the un-necked material. This differs from stretching/orienting a material layer, during which the layer is thinned and the basis weight is permanently reduced.

Typically, such necked nonwoven fabric materials are capable of being necked up to about 80 percent. For example, the extensible outer cover 20 may be provided by a material that has been necked from about 10 to about 80 percent, desirably from about 20 to about 60 percent, and more desirably from about 30 to about 50 percent for improved performance. For the purposes of the present disclosure, the term "percent necked" or "percent neckdown" refers to a ratio or percentage determined by measuring the difference between the pre-necked dimension and the necked dimension of a neckable material, and then dividing that difference by the pre-necked dimension of the neckable material and multiplying by 100 for percentage. The percent necked can be determined in accordance with the description in the above-mentioned U.S. Pat. No. 4,965,122.

The extensible outer cover 20 is made from a necked laminate material to provide the desired levels of extensibility as well as liquid impermeability and vapor permeability. Desirably, both the neckable fabric and the film material are nonelastic materials for increased permanent set, reduced cost and improved manufacturing efficiency. Suitable necked laminates that include at least one non-elastic neckable material laminated to at least one non-elastic film material are described in U.S. patent application Ser. No. 09/455,513 filed Dec. 6, 1999 and entitled "TRANSVERSELY EXTENSIBLE AND RETRACTABLE NECKED LAMINATE OF NON-ELASTIC SHEET LAYERS", the entire disclosure of which is hereby incorporated by reference.

The extensible inner layer 42 can be made from either cast or blown film equipment, can be coextruded and can be embossed if so desired. The inner layer 42 may be made from any suitable non-elastic polymer composition and may include multiple layers. The inner layer 42 can also be breathable. For example, the inner layer 42 may contain such fillers as micropore developing fillers, e.g. calcium carbonate; opacifying agents, e.g. titanium dioxide; and antiblock additives, e.g. diatomaceous earth. Suitable polymers for the inner layer 42 include but are not limited to non-elastic extrudable polymers such as polyolefin or a blend of polyolefins, nylon, polyester and ethylene vinyl alcohol. More particularly, useful polyolefins include polypropylene and polyethylene. Other useful polymers include those described in U.S. Pat. No. 4,777,073 to Sheth, assigned to Exxon Chemical Patents Inc., such as a copolymer of polypropylene and low density polyethylene or linear low density polyethylene.

Alternative polymers for the inner layer 42 include those referred to as single site catalyzed polymers such as "metallocene" polymers produced according to a metallocene process and which have limited elastic properties. The term "metallocene-catalyzed polymers" as used herein includes those polymer materials that are produced by the polymerization of at least ethylene using metallocenes or constrained geometry catalysts, a class of organometallic complexes, as catalysts. For example, a common metallocene is ferrocene, a complex of a metal between two cyclopentadienyl (Cp) ligands. Such metallocene polymers are available from Exxon Chemical Company of Baytown, Tex. under the trade name EXXPOL® for polypropylene based polymers and EXACT® for polyethylene based polymers and from Dow Chemical Company of Midland, Mich. under the name ENGAGE®. Preferably, the metallocene polymers are selected from copolymers of ethylene and 1-butene, copolymers of ethylene and 1-hexene, copolymers of ethylene and 1-octene and combinations thereof.

Suitable neckable materials for the outer layer 40 include nonwoven webs, woven materials and knitted materials such as those described in the above-mentioned U.S. Pat No. 4,965,122. Nonwoven fabrics or webs have been formed from many processes, for example, bonded carded web processes, meltblowing processes and spunbonding processes. The nonelastic neckable material is preferably formed from at least one member selected from fibers and filaments of inelastic polymers. Such polymers include polyesters, for example, polyethylene terephthalate, polyolefins, for example, polyethylene and polypropylene, polyamides, for example, nylon 6 and nylon 66. These fibers or filaments are used alone or in a mixture of two or more thereof. Suitable fibers for forming the neckable material include natural and synthetic fibers as well as bicomponent, multi-component, and shaped polymer fibers. Many polyolefins are available for fiber production according to the present invention, for example, fiber forming polypropylenes include Exxon Chemical Company's EscoreneO PD 3445 polypropylene and Himont Chemical Company's PF-304. Polyethylenes such as Dow Chemical's ASPUNO 6811A linear low density polyethylene, 2553 LLDPE and 25355 and 12350 high density polyethylene are also suitable polymers. The nonwoven web layer may be bonded to impart a discrete bond pattern with a prescribed bond surface area. If too much bond area is present on the neckable material, it will break before it necks. If there is not enough bond area, then the neckable material will pull apart. Typically, the percent bonding area useful in the present invention ranges from around 5 percent to around 40 percent of the area of the neckable material.

The inner layer 42 may be laminated to the neckable material of the outer layer 40 to form the laminate by conventional methods known in the art including adhesive bonding, point bonding, thermal point bonding, and sonic welding. The laminate is then necked by conventional necking processes that typically vary the surface speed of the web to draw or neck the laminate. Such necking provides striated rugosities in the film and/or laminate resulting in transverse extensibility and retractability to the necked laminate and more "cloth-like" aesthetics. It is known that stretching and orienting a filled film layer (inner layer 42) causes micropores to form in the film, but longitudinal striated rugosities do not typically form in the film layer when stretched. The film layer would instead become physically thinner and may narrow slightly. By necking the laminate, the non-elastic neckable material, which is attached to the non-elastic film layer, will neck and bring the non-elastic film layer with it, thereby forming the longitudinal striated rugosities in the film which allow the film layer to extend in the transverse direction.

Alternative necked laminate materials that could be used to provide the outer cover 20 of the different aspects of the present invention are described in U.S. patent application Ser. No. 09/460,490 filed Dec. 14, 1999 and entitled "BREATHABLE LAMINATE PERMANENTLY CONFORMABLE TO THE CONTOURS OF A WEARER", the entire disclosure of which is hereby incorporated by reference.

The absorbent body 24 should be capable of moving with the outer cover 20 as it stretches. The absorbent body 24 may have any of a number of shapes, including rectangular, I-shaped, or T-shaped. It is generally preferred that the absorbent body 24 is narrower in the crotch region than in the front or posterior regions of the diaper 10. As illustrated herein, the absorbent body 24 is generally T-shaped with the laterally extending cross-bar of the "T" generally corresponding to the anterior region 12 of the absorbent article for improved performance, especially for male infants. The size and the absorbent capacity of absorbent body 24 will be selected according to the size of the intended wearer and the liquid loading imparted by the intended use of the absorbent article. Further, the size and the absorbent capacity of the absorbent body 24 can be varied to accommodate wearers ranging from infants through adults. In addition, it has been found that the densities and/or basis weights of the absorbent body 24 can be varied. In the embodiment described herein, the central absorbent layer 31 of the absorbent body 24 has an absorbent capacity of at least about 300 grams of synthetic urine.

Various types of wettable, hydrophilic fibrous material can be used to form part of absorbent body 24. Examples of suitable fibers include naturally occurring organic fibers composed of intrinsically wettable material, such as cellulose fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

The central absorbent layer 31 of the absorbent body 24 may include a combination of hydrophilic fibers and high-absorbency material. However, it is to be understood that absorbent bodies having absorbent layers of other compositions and having dimensions other than described can be used without departing from the scope of the present invention. More specifically, the high-absorbency material in the central absorbent layer 31 can be selected from natural, synthetic, and modified natural polymers and materials. The high-absorbency materials can be inorganic materials, such as silica gels, or organic compounds, such as crosslinked polymers. The term "crosslinked" refers to methods for effectively rendering normally water-soluble materials substantially water insoluble but swellable. Such methods include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly(acrylamides), poly(vinyl ethers), maleic anhydride copolymers with vinyl ethers and alpha-olefins, poly(vinyl pyrrolidone), poly(vinyl morpholinone), poly(vinyl alcohol), and mixtures and copolymers thereof. Further polymers suitable for use in the central absorbent layer 31 of the absorbent body 24 include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum, and the like. Mixtures of natural and wholly or partially synthetic absorbent polymers can also be useful in the present invention.

The high absorbency material may be in any of a wide variety of geometric forms. As a general rule, it is preferred that the high absorbency material be in the form of discrete particles or beads. However, the high absorbency material may also be in the form of fibers, flakes, rods, spheres, needles, or the like. In general, the high absorbency material is present in the central layer 31 of the absorbent body 24 in an amount of from about 5 to about 90 percent by weight, desirably in an amount of at least about 30 percent by weight, and even more desirably in an amount of at least about 50 percent by weight based on a total weight of the central layer 31. For example, the central absorbent layer 31 may include a laminate which includes at least about 50 percent by weight and desirably at least about 70 percent by weight of high-absorbency material overwrapped by a fibrous web (not shown) or other suitable material for maintaining the high-absorbency material in a localized area.

An example of high-absorbency material suitable for use in the present invention is SANWET IM 3900 polymer available from Hoechst Celanese, a business having offices in Portsmouth, Va. Other suitable superabsorbents may include FAVOR SXM 880 polymer obtained from Stockhausen, a business having offices in Greensboro, N.C. Optionally, a substantially hydrophilic tissue wrapsheet (not shown) may be employed to help maintain the integrity of the structure of the absorbent body 24. The tissue wrapsheet is typically placed about the absorbent body 24 over at least the two major facing surfaces thereof. The tissue wrapsheet can be made of an absorbent cellulosic material, such as creped wadding or a high wet-strength tissue. The tissue wrapsheet can be configured to provide a wicking layer that helps to rapidly distribute liquid over the mass of absorbent fibers constituting the central absorbent layer 31 of the absorbent body 24.

Due to the thinness of central absorbent layer 31 of the absorbent body 24 and the high absorbency material within the central absorbent layer, the liquid uptake rates of the central absorbent layer, by itself, may be too low, or may not be adequately sustained over multiple insults of liquid into the absorbent body. To improve the overall liquid uptake and air exchange, the absorbent body 24 includes the porous, liquid-permeable layer 34 of surge management material. The surge management layer 34 is typically less hydrophilic than the central absorbent layer 31, and has an operable level of density and basis weight to quickly collect and temporarily hold liquid surges, to transport the liquid from its initial entrance point and to substantially completely release the liquid to other parts of the central absorbent layer 31. This configuration can help prevent the liquid from pooling and collecting on the portion of the diaper 10 positioned against the wearer's skin, thereby reducing the feeling of wetness by the wearer. The structure of the surge management layer 34 also generally enhances the air exchange within the diaper 10.

Various woven and nonwoven fabrics can be used to construct the surge management layer 34. For example, the surge management layer 34 may be a layer made of a meltblown or spunbond web of synthetic fibers, such as polyolefin fibers. The surge management layer 34 may also be a bonded-carded-web or an airlaid web composed of natural and synthetic fibers. The bonded-carded-web may, for example, be a thermally bonded web that is bonded using low melt binder fibers, powder or adhesive. The webs can optionally include a mixture of different fibers. The surge management layer 34 may be composed of a substantially hydrophobic material, and the hydrophobic material may optionally be treated with a surfactant or otherwise processed to impart a desired level of wettability and hydrophilicity. As one example, the surge management layer 34 includes a hydrophobic, nonwoven material having a basis weight of from about 30 to about 120 grams per square meter.

The central absorbent layer 31 of the absorbent body 24 is positioned in liquid communication with surge management layer 34 to receive liquids released from the surge management layer 34, and to hold and store the liquid. In the illustrated embodiment, the surge management layer 34 is a separate layer positioned over the central absorbent layer 31 of the absorbent body 24. The surge management layer 34 serves to quickly collect and temporarily hold discharged liquids, to transport such liquids from the point of initial contact and spread the liquid to other parts of the surge management layer 34, and then to substantially completely release such liquids into the central absorbent layer 31 of the absorbent body 24.

The surge management layer 34 can be of any desired shape. Suitable shapes include for example, circular, rectangular, triangular, trapezoidal, oblong, dog-boned, hourglass-shaped, or oval. In the illustrated embodiment, the surge management layer 34 is coextensive with the central absorbent layer 31 of the absorbent body 24. Alternatively, the surge management layer 34 may extend over only a part of the central absorbent layer 31. Where the surge management layer 34 extends only partially along the length of the central absorbent layer 31, the surge management layer 34 may be selectively positioned anywhere along the central layer. For example, the surge management layer 34 may function more efficiently when it is offset toward the anterior region 12 of the diaper 10. The surge management layer 34 may also be approximately centered about the longitudinal center line of the central absorbent layer 31 of the absorbent body 24.

Additional materials suitable for the surge management layer 34 are set forth in U.S. Pat. No. 5,486,166 issued Jan. 23, 1996 in the name of C. Ellis et al. and entitled "FIBROUS NONWOVEN WEB SURGE LAYER FOR PERSONAL CARE ABSORBENT ARTICLES AND THE LIKE"; U.S. Pat. No. 5,490,846 issued Feb. 13, 1996 in the name of Ellis et al. and entitled "IMPROVED SURGE MANAGEMENT FIBROUS NONWOVEN WEB FOR PERSONAL CARE ABSORBENT ARTICLES AND THE LIKE"; and U.S. Pat. No. 5,364,382 issued Nov. 15, 1994 in the name of Latimer et al. and entitled "ABSORBENT STRUCTURE HAVING IMPROVED FLUID SURGE MANAGEMENT AND PRODUCT INCORPORATING SAME", the disclosures of which are hereby incorporated by reference.

Referring again to FIG. 4, the ventilation layer 32 of the absorbent body 24 is located between the outer cover 20 and the central absorbent layer 31 of the absorbent body 24. The ventilation layer 32 serves to facilitate the movement of air within and through the diaper 10 and prevent the outer cover 20 from being in surface to surface contact with at least a portion of the absorbent body 24. Specifically, the ventilation layer 32 serves as a conduit through which air and water vapor can move from the absorbent body 24 through the vapor permeable outer cover 20.

The ventilation layer 32 may be formed from materials described above as being suitable for the surge management layer 34 such as nonwoven, (e.g., spunbond, meltblown or carded), woven, or knitted fibrous webs composed of natural fibers and/or synthetic polymeric fibers. Suitable fibers include, for example, acrylic fibers, polyolefin fibers, polyester fibers, or blends thereof. The ventilation layer 32 may also be formed from a porous foam material such as an open-celled polyolefin foam, a reticulated polyurethane foam, and the like. The ventilation layer 32 may include a single layer of material (as shown) or a composite of two or more layers of material. As one example, the ventilation layer 32 includes a hydrophobic, nonwoven material having a thickness of at least about 0.10 centimeters determined under a restraining pressure of 0.05 psi (0.34 kPa) and a basis weight of from about 20 to about 120 grams per square meter. However, the ventilation layer 32 may comprise a bonded-carded-web, nonwoven fabric that includes bicomponent fibers and that has an overall basis weight of about 83 grams per square meter. The ventilation layer 32 can be a homogeneous blend of about 60 weight percent polyethylene/polyester (PE/PET), sheath-core bicomponent fibers that have a fiber denier of about 3 d and about 40 weight percent single component polyester fibers that have a fiber denier of about 6 d and that have fiber lengths of from about 3.8 to about 5.08 centimeters.

The ventilation layer 32 can be of any desired shape. Suitable shapes include, for example, circular, rectangular, triangular, trapezoidal, oblong, dog-boned, hourglass-shaped, or oval. The ventilation layer 32 may extend beyond, completely over or partially over the central absorbent layer 31 of the absorbent body 24. For example, the ventilation layer 32 may suitably be located over the crotch region 16 of the diaper 10 and be substantially centered side-to-side with respect to the lateral direction 38 of the diaper 10. It is generally desired that the entire absorbent body 24 be underlaid with the ventilation layer 32 to prevent substantially all surface to surface contact between the outer cover 20 and the central absorbent layer 31. In the illustrated embodiment, the ventilation layer 32 is coextensive with the central absorbent layer 31. This allows for the maximum degree of air exchange with minimal dampness on the garment facing surface of the outer cover 20.

The ventilation layer 32 is arranged in a direct, contacting liquid communication with the central absorbent layer 31 of the absorbent body 24. The ventilation layer 32 may be operably connected to the outer cover 20 with a conventional pattern of adhesive, such as a swirl adhesive pattern. In addition, the ventilation layer 32 may be operably connected to the central absorbent layer 31 with a conventional pattern of adhesive. The amount of adhesive add-on should be sufficient to provide the desired levels of bonding, but should be low enough to avoid excessively restricting the movement of air and vapor from the central absorbent layer 31 and through the outer cover 20.

The ventilation layer 32 may further serve to quickly collect and temporarily hold discharged liquids, which pass through the central absorbent layer 31 of the absorbent body 24. The ventilation layer 32 may then transport such liquids from the point of initial contact and spread the liquid to other parts of the ventilation layer 32, and then substantially completely release such liquids back into the central absorbent layer 31. Thus, in the illustrated embodiment, the absorbent body 24 includes three layers. It is to be understood that although preferred, the ventilation layer 32 and surge management layer 34 may be omitted from the absorbent body 24 without departing from the scope of the present invention.

The bodyside liner 22 is in superposed relation to the outer cover 20. The absorbent body 24 is located between the bodyside liner 22 and the outer cover 20. The bodyside liner 22 includes a top sheet 48 which is preferably pliable, soft feeling, and nonirritating to the wearer's skin, and is employed to help isolate the wearer's skin from the absorbent body 24. The top sheet 48 is less hydrophilic than the absorbent body 24, to present a relatively dry surface to the wearer, and is sufficiently porous to be liquid permeable, permitting liquid to readily penetrate through its thickness. A suitable top sheet 48 may be manufactured from a wide selection of web materials, but is preferably capable of stretching in at least one direction (e.g., the longitudinal or lateral direction 36 or 38). Various woven and nonwoven fabrics including either or both synthetic and natural fibers can be used for the top sheet 48. For example, the bodyside liner may be composed of a meltblown or spunbonded web of the desired fibers, and may also be a bonded-carded-web. Layers of different materials that may have different fiber deniers can also be used. The various fabrics can be composed of natural fibers, synthetic fibers or combinations thereof. The top sheet 48 of the bodyside liner 32 may be composed of a substantially hydrophobic material, and the hydrophobic material may optionally be treated with a surfactant or otherwise processed to impart a desired level of wettability and hydrophilicity. Examples of suitable materials for the top sheet 48 of the bodyside liner 22 include 0.3-0.5 osy (10-17 gsm) polypropylene spun bond web treated with a suitable wettability treatment, 0.3-0.5 osy (10-17 gsm) bonded carded web and 0.4-0.8 osy (14-27 gsm)

thru air bonded carded web. The fabric can be surface treated with an operative amount of surfactant, such as about 0.28 percent Triton X-102 surfactant. The surfactant can be applied by any conventional means, such as spraying, printing, brush coating or the like.

In particular embodiments, the top sheet 48 is desirably extensible such that it is capable of extending with the outer cover 20 to assist in providing the improved fastening, fit and containment discussed above. For example, the top sheet 48 can be composed of various extensible materials such as a necked fabric, a creped fabric, a micro-pleated fabric, perforated polymer films or the like, as well as combinations thereof. The fabrics may be woven or nonwoven materials, such as spunbond fabrics, that may be elastic or non-elastic. Examples of suitable manufacturing techniques and suitable necked nonwoven fabric materials for such an extensible top sheet 48 are described in U.S. Pat No. 4,965,122 entitled REVERSIBLY NECKED MATERIAL, by M. T. Morman which issued Oct. 23, 1990.

Desirably, the top sheet 48 is made from non-elastic neckable materials for reduced cost and improved manufacturing efficiency. Suitable non-elastic neckable materials for such a configuration include nonwoven webs, woven materials and knitted materials. Such webs can include one or more fabric layers. Nonwoven fabrics or webs have been formed from many processes, for example, bonded carded web processes, meltblowing processes and spunbonding processes. The non-elastic neckable material is preferably formed from at least one member selected from fibers and filaments of inelastic polymers. Such polymers include polyesters, for example, polyethylene terephthalate, polyolefins, for example, polyethylene and polypropylene, polyamides. These fibers or filaments are used alone or in a mixture of two or more thereof. Suitable fibers for forming the neckable material include natural and synthetic fibers as well as bicomponent, multi-component, and shaped polymer fibers. Many polyolefins are available for fiber production according to the present invention, for example, fiber forming polypropylenes include Exxon Chemical Company's Escorene PD 3445 polypropylene and Himont Chemical Company's PF-304. Polyethylenes such as Dow Chemical's ASPUN® 6811A linear low density polyethylene, 2553 LLDPE and 25355 and 12350 high density polyethylene are also suitable polymers.

The neckable material may be necked to form the extensible top sheet 48 by conventional necking processes that typically vary the surface speed of the web to draw or neck the material. Such necking will allow the material to extend and retract in the transverse direction. As discussed above, such necked nonwoven fabric materials typically are capable of being necked up to about 80 percent. For example, the extensible top sheet 48 of the various aspects of the present invention may be necked from about 10 to about 80 percent, desirably from about 20 to about 60 percent, and more desirably from about 30 to about 50 percent for improved performance.

To obtain the a satisfactory stretching of the top sheet 48 of the bodyside liner 22, the top sheet 48 may be subject to a mechanical process, such as necking, creping or corrugating. The mechanical process is preferably performed so that stretching in the lateral direction 38 is facilitated. In a preferred embodiment, stretching and retraction in the longitudinal direction are achieved by a suspension arranged to resiliently oppose stretching of the top sheet 48. In the illustrated embodiment, the suspension comprises a series of cords 50 attached in a suitable manner, such as by lines of 1-5 gsm elastic attachment adhesive 52 to the underside of the remainder of the bodyside liner 22. The adhesive may be applied in a patterned layer, a sprayed pattern or an array of separate lines, swirls or spots. The cords 50 may also be bonded to the top sheet 48 with thermal bonds and/or sonic bonds. It is envisioned that the cords 50 may be attached to the top sheet 48 along less than their full lengths. More particularly in one preferred embodiment (not shown), the cords 50 are bonded to the top sheet 48 only at the ends of the cords, leaving the middle sections of the cords free of attachment to the top sheet. The cords 50 are shown in FIG. 1 broken at different lengths, but all have substantially the same length. It is to be understood that the cords 50 may have different lengths without departing from the scope of the present invention. The cords 50 extend lengthwise of the bodyside liner from the anterior region 12 to the posterior region 14 passing through the crotch region 16. The cords 50 are in parallel, spaced apart relation with each other, and preferably made of a material which permits elongation of the cords along their lengths. Suitable stranded elastic laminates for the cords 50 include a styrene-butadiene elastomer sold under the trademark Kraton® and a spandex fiber in the form of continuous microfilaments sold under the trademark Lycra®.

Although use of the elastic cords 50 is preferred, it is envisioned that a bodyside liner (not shown) could be made to resiliently stretch without such cords. For instance, the top sheet 48 could be formed with an elastic fiber in the matrix of the material. Similarly, latent elastic strands could be formed in the top sheet 48 and activated in the production process such as through the application of heat or microwaves to shrink, producing a manufactured in gap between the bodyside liner and the absorbent pad. Moreover, a single cord 50 could be used, or another structure separate from the top sheet 48, such as a thin, flat elastic strap (not shown).

The bodyside liner 22, including the top sheet 48 and adhered cords 50 can be stretched at least about 30% of its original length, more preferably at least about 50% of its original length and most preferably about 80% of its original length. The maximum stretch of the bodyside liner is preferably no more than about 200% of its original length, more preferably about 150% of its original length and most preferably about 120% of its original length. The force required to produce stretching (measured at 50% of maximum stretching of the bodyside liner) is preferably in the range of about 30 to 500 g/in, more preferably in the range of about 50 to 300 g/in and most preferably in the range of about 60 to 150 g/in. It is desirable for the bodyside liner to exert a retraction force (i.e., a force in opposition to stretching of the bodyside liner). In a preferred embodiment, the bodyside liner exerts a retraction force in the range of about 30% to 80% of the minimum extension force necessary to produce further stretching of the liner at 50% elongation. More preferably, the retraction force is about 60% to 80% of the minimum extension force.

Figure 2:
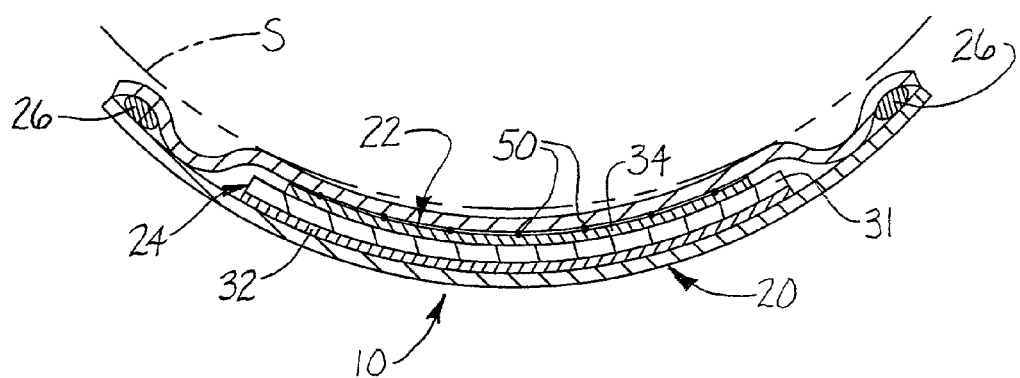
FIG. 2 is a fragmentary cross section generally taken in the plane including line 2-2 of FIG. 1, but illustrating a crotch region of the diaper as worn.

The outer cover 20 should have the ability to stretch which is preferably at least equal to that of the bodyside liner 22. In cases where the ability to stretch is roughly equal, the outer cover 20 should have a lesser ability or no ability to retract after being stretched. Stated another way, the bodyside liner 22 is relatively more resilient than the outer cover 20. In a preferred embodiment, the outer cover 20 may be purely extensible or only weakly elastic so that in normal use, the material of the outer cover would not significantly retract from its stretched configuration. In this same embodiment, the bodyside liner 22 is sufficiently elastic to have at least some movement toward the original dimensions of the liner after relief or reduction of the force which produced the stretching. Thus, the diaper 10 of the illustrated embodiment is constructed to produce separation of the bodyside liner 22 from the outer cover 20 and absorbent body 24 as the absorbent body takes on liquid waste. Referring to FIG. 2, it may be seen than in its original state, the diaper 10 has substantially no separation between the surge management layer 34 and the bodyside liner 22. However, it is to be understood that there could be some initial (i.e., before the bodyside liner 22 has absorbed any liquid) separation without departing from the scope of the present invention. When put on the child, the ability of both the outer cover 20 and bodyside liner 22 to stretch allows the diaper 10 to comfortably conform to the infant's body. Stretching helps to avoid tearing the fasteners 30 when the diaper 10 is put on. Stretching further inhibits tearing of the bodyside liner 22 which could cause leakage of superabsorbent gel beads. Moreover, stretching of inextensible material of an outer cover causes weakening of the outer cover.

Figure 3:
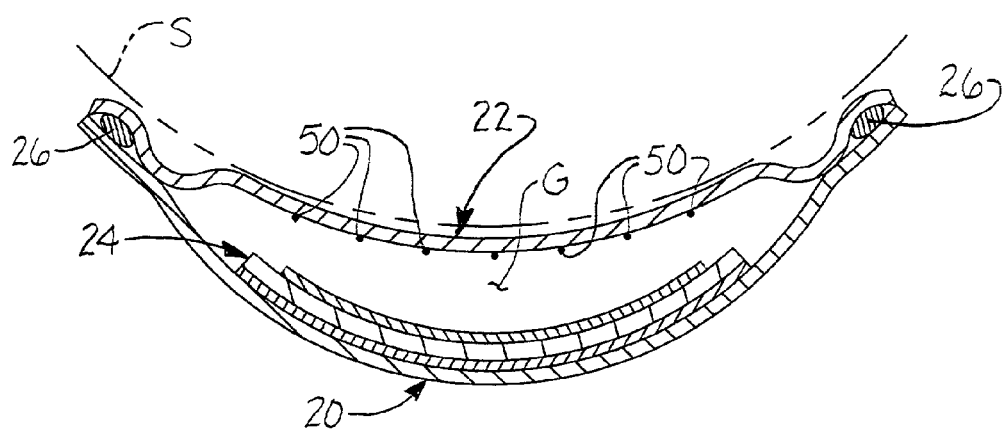
FIG. 3 is the cross section of FIG. 2, but illustrating the diaper after having received an insult which is absorbed by an absorbent pad of the diaper.

Upon receiving an insult, particularly in the form of urine, liquid flows through the permeable bodyside liner 22 to the surge management layer 34 of the absorbent body 24. The bodyside liner 22, may or may not stretch at this time, but its resiliency will keep it closely proximate to or in contact with the child's skin. The surge management layer 34 passes the liquid onto the central absorbent layer 31 in which the urine is absorbed and held. The weight of the absorbent body 24 increases by the weight of the urine absorbed and creating a downward load against the outer cover 20. The outer cover is constructed to stretch under such a load, allowing the outer cover 20 and absorbent body 24 to sag down away from the lower torso of the child, as is shown in FIG. 3. However, it may be seen that the bodyside liner 22 remains close to the child's skin S so that a separation of the bodyside liner from the absorbent body 24 occurs creating a gap G. The presence of the gap G separates the child's skin S from the moisture in the absorbent body 24 to promote dryness in the first instance. Second, the air gap G is believed to allow better circulation of air and vapor to and from the child's skin S through the bodyside liner 22. As a result the skin S is able to remain dryer, promoting skin health. It is preferred that the outer cover 20 and absorbent body 24 be sufficiently breathable to permit air to pass through into and out of the air gap G. However, the bodyside liner 22 remains close to or in contact with the child's skin S to help prevent leakage from the diaper 10.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

We claim:

1. An absorbent article comprising:
   an outer cover adapted to stretch upon application of a load by a first amount;
   a liquid and vapor permeable bodyside liner defining a bodyfacing surface and being generally superposed and coextensive with the outer cover, the bodyside liner being adapted to stretch upon application of the load by a second amount, said bodyside liner comprising a sheet of liquid and vapor permeable material and a suspension arranged to resiliently oppose stretching of the bodyside liner;
   an absorbent body located between the bodyside liner and the outer cover and generally movable with the outer cover upon stretching of the outer cover; and
   said first amount of stretch of the outer cover being greater than said second amount of stretch of the bodyside liner whereby a gap is formed between the bodyside liner and the absorbent body facilitating the flow of air and vapor through the bodyside liner in a loaded condition of the absorbent body, the bodyside liner being relatively more resilient when stretched than the outer cover.

2. An absorbent article as set forth in claim 1 wherein the suspension is adapted to retract the bodyside liner subsequent to stretching of the bodyside liner.

3. An absorbent article as set forth in claim 1 wherein the suspension comprises at least one elastic cord located between the bodyside liner and the absorbent body, the elastic cord being stretched axially upon stretching of the bodyside liner.

4. An absorbent article as set forth in claim 3 wherein the suspension comprises multiple cords arranged in parallel, spaced apart relation to each other.

5. An absorbent article as set forth in claim 3 wherein the absorbent article comprises a garment worn to capture waste from the human body, the garment including an anterior region, a posterior region and a crotch region disposed longitudinally therebetween, said anterior region, posterior region and crotch region being integrally formed and configured when worn to define a central waist opening and a pair of leg openings, the crotch region extending generally laterally between said leg openings and wherein the cord extends lengthwise generally parallel to line extending from the anterior region to the posterior region.

6. An absorbent article as set forth in claim 5 wherein the cord is attached to the bodyside liner by adhesive.

7. An absorbent article as set forth in claim 5 wherein the bodyside liner is free of fixed connection to the outer cover and absorbent body at least in the crotch region.

8. An absorbent article as set forth in claim 3 wherein the cord is made of a material selected from a group including a styrene-butadiene elastomer and a spandex fiber in the form of continuous microfilaments.

9. An absorbent garment for capturing human waste when worn, the garment comprising:
   a liquid impermeable outer cover adapted to stretch upon application of a load by a first amount;
   a liquid and vapor permeable bodyside liner generally superposed and coextensive with the outer cover, the bodyside liner being adapted to stretch upon application of the load by a second amount, the bodyside liner comprising a stretchable sheet of liquid and vapor permeable material defining a bodyfacing surface, and plural cords of resilient elastic material on a side of the sheet opposite the bodyfacing surface, the cords applying a resilient force in opposition to stretching of the sheet;
   an absorbent body located between the bodyside liner and the outer cover and generally movable with the outer cover upon stretching of the outer cover; and
   said first amount of stretch of the outer cover being greater than said second amount of stretch of the bodyside liner whereby a gap is formed between the bodyside liner and the absorbent body facilitating the flow of air and vapor through the bodyside liner in a loaded condition of the absorbent body.

10. An absorbent garment as set forth in claim 9 wherein the absorbent garment includes an anterior region, a posterior region and a crotch region disposed longitudinally therebetween, said anterior region, posterior region and crotch region being integrally formed and configured when worn to define a central waist opening and a pair of leg openings, the crotch region extending generally laterally between said leg openings and wherein the cords extend lengthwise generally parallel to line extending from the anterior region to the posterior region.

11. An absorbent garment as set forth in claim 10 wherein the cords are attached to the bodyside liner by adhesive.

12. An absorbent garment as set forth in claim 10 wherein the bodyside liner is free of fixed connection to the outer cover and absorbent body at least in the crotch region.

13. An absorbent garment as set forth in claim 9 wherein the cord is made of a material selected from a group including a styrene-butadiene elastomer and a spandex fiber in the form of continuous microfilaments.

14. An absorbent garment as set forth in claim 9 wherein the bodyside liner is adapted to stretch in a range from about 30% to about 200% of its original length.

15. An absorbent garment as set forth in claim 14 wherein the bodyside liner is adapted to stretch in a range from about 50% to about 150% of its original length.

16. An absorbent garment as set forth in claim 15 wherein the bodyside liner is adapted to stretch in a range from about 80% to about 120% of its original length.

17. An absorbent garment as set forth in claim 9 wherein the bodyside liner will further stretch at 50% of its maximum extension upon application of a load of at least about 30 g/in.

18. An absorbent garment as set forth in claim 17 wherein the bodyside liner will further stretch at 50% of its maximum extension upon application of a load of at least about 50 g/in.

19. An absorbent garment as set forth in claim 18 wherein the bodyside liner will further stretch at 50% of its maximum extension upon application of a load of at least about 60 g/in.

20. An absorbent garment as set forth in claim 19 wherein the bodyside liner will further stretch at 50% of its maximum extension upon application of a load less than about 150 g/in.

21. An absorbent garment as set forth in claim 9 wherein the bodyside liner has a retraction force at 50% of its maximum extension of at least about 9 g/in.

22. An absorbent garment as set forth in claim 21 wherein the bodyside liner has an retraction force at 50% of its maximum extension of at least about 15 g/in.

23. An absorbent garment as set forth in claim 22 wherein the bodyside liner has an retraction force at 50% of its maximum extension of at least about 18 g/in.

24. An absorbent garment as set forth in claim $\leq$ wherein the bodyside liner has an retraction force at 50% of its maximum extension of less than about 120 g/in.

25. An absorbent garment as set forth in claim 9 wherein the garment is free of material on the side of the bodyside liner opposite the absorbent body and between the bodyside liner and the absorbent body.

* * * * *

UNITED STATES PATENT AND TRADEMARK OFFICE
CERTIFICATE OF CORRECTION

PATENT NO. : 7,438,707 B2
APPLICATION NO. : 10/035650
DATED : October 21, 2008
INVENTOR(S) : Bushman et al.

It is certified that error appears in the above-identified patent and that said Letters Patent is hereby corrected as shown below:

In Claim 24, column 20, line 19, delete "≦" and insert therefor -- 23 --.

Signed and Sealed this

Twenty-sixth Day of January, 2010

David J. Kappos
*Director of the United States Patent and Trademark Office*